United States Patent [19]

Carli et al.

[11] Patent Number: 5,582,836

[45] Date of Patent: Dec. 10, 1996

[54] TRANSDERMAL THERAPEUTIC COMPOSITIONS

[75] Inventors: Fabio Carli; Luca Dobetti, both of Trieste, Italy

[73] Assignee: Vectorpharma International S.p.A., Trieste, Italy

[21] Appl. No.: 777,123

[22] Filed: Oct. 16, 1991

[30] Foreign Application Priority Data

Oct. 17, 1990 [IT] Italy ..................... 21766/90

[51] Int. Cl.⁶ ..................... A61F 13/02; A61F 13/00
[52] U.S. Cl. ............... 424/449; 424/447; 424/448
[58] Field of Search ..................... 424/449, 448, 424/447

[56] References Cited

U.S. PATENT DOCUMENTS

| | | | |
|---|---|---|---|
| 3,797,494 | 3/1974 | Zaffaroni | 128/268 |
| 4,749,574 | 6/1988 | Ueda et al. | 424/448 |
| 4,818,540 | 4/1989 | Chien et al. | 424/449 |
| 4,946,870 | 8/1990 | Partain, III et al. | 424/449 |
| 5,001,139 | 3/1991 | Lawter | 424/449 |
| 5,002,773 | 3/1991 | Keshary et al. | 424/449 |
| 5,028,435 | 7/1991 | Katz et al. | 424/484 |
| 5,045,319 | 9/1991 | Chien et al. | 424/449 |
| 5,051,426 | 9/1991 | Parnell | 514/811 |

FOREIGN PATENT DOCUMENTS

| | | |
|---|---|---|
| 0200562 | 11/1986 | European Pat. Off. . |
| 0336014 | 10/1989 | European Pat. Off. . |
| 0364944 | 4/1990 | European Pat. Off. . |
| 0371431 | 6/1990 | European Pat. Off. . |
| 0399765 | 11/1990 | European Pat. Off. . |

*Primary Examiner*—Jyothsna Venkat
*Attorney, Agent, or Firm*—Birch, Stewart, Kolasch & Birch, LLP

[57] ABSTRACT

There are described transdermal therapeutic compositions showing an improved shelf stability of the chemical-physical structure of the medicament and particularly useful for its cutaneous administration, said compositions consisting of a supporting rigid sheet, a polymetic matrix and a protective removable sheet, wherein said polymeric matrix consists of a polymeric film in which there are distributed particles loaded with medicaments and agents promoting the cutaneous absorption.

19 Claims, 1 Drawing Sheet

TRANSDERMAL THERAPEUTIC COMPOSITIONS

DESCRIPTION

1. Technical Field of the Invention

The present invention relates to transdermal therapeutic compositions consisting of a supporting rigid film, a reserve matrix, an optional adhesive layer and a protective removable sheet, wherein the reserve matrix consists of a polymeric adhesive or non-adhesive film in which there are distributed microporous particles or polymeric microspheres loaded with medicaments and/or agents promoting medicament absorption and to process for preparing the same.

2. Background of the Invention

Transdermal systems comprising particles of materials different from the continuous matrix and loaded with a medicament have already been described.

The U.S. Pat. No. 4,778,678 discloses transdermal systems wherein the medicament glyceroltrinitrate is deposited onto the surface of lactose particles and the thus obtained powder is thereafter dispersed within the matrix of the filmogenic polymer according to a co-milling technique, in order to achieve the highest homogeneity of distribution. Most frequently, the microparticles distributed within the dispersing matrix consist of polymeric material.

The U.S. Pat. No. 4,624,665 describes systems wherein particles consisting essentially of hydrophobic, biodegradable, linear polymers, such as polylactic or polyglycolic acid or co-polymers thereof, are dispersed within a viscous liquid, such as VASELIN, polyethyeneglycol, glycerin, etc. which represents the "reserve" of the same transdermal system. The microparticles are prepared by co-precipitation in an emulsion.

Continuous polymeric matrixes containing microspheres constituted, inter alia, of biodegradable polymers, are also suggested in the U.S. Pat. No. 4,898,734. In any case both the polymers of the continuous matrix and of the microspheres are linear and hydrophobic in type. The U.S. Pat. No. 4,749,574 discloses the use of microparticles of 2-nitroxymethyl-6-chloropyridine distributed in a transdermal system of siliconic polymers, or hydrogels, or methacrylates, or cellulose, etc. In such systems the microparticles are constituted by actual microcapsules, prepared according to conventional techniques for coating drug-loaded inert beads with insoluble polymers (such as ethylcellulose, acrylic/methacrylic esters. ect.). According to all the previous patents, the main purpose of distributing polymeric microspheres within a continuous polymeric matrix was that of controlling and/or delaying the release; this is highlighted by the fact that the microsphere polymeric materials were essentially hydrophobic in nature.

For instance the patents JP 59/104314 and DE-A-3 333 240 describe the addition of hydrophylic polymeric gels within the filmogenic siliconic polymeric mass of transdermal systems. In such systems the active agent is not adsorbed on the gels but merely dissolved in the mixture of gel and filmogenic polymer.

The patent application EP-A-0 186 019 discloses transdermal systems wherein to the mass of filmogenic polymer constituted by gum and adhesive. polysaccharide polymers (such as galactomannan or cellulose) are added, which show no drug supporting function but merely modulate the hydrophilic feature of the transdermal matrix in its entirety. Finally the EP-A-0 328 145 describes hydrophobic crosslinked polymeric particles (polystyrene - polydivinylbenzene) which are distributed within plastic materials, not however in specific transdermal films.

DETAILED DESCRIPTION OF THE INVENTION

Unlike the matter so far disclosed, the object of the present invention is prepare continuous polymeric matrices for transdermal application, comprising crosslinked polymeric microspheres essentially hydrophilic/amphiphilic in nature, suitable for loading medicaments and agents promoting cutaneous absorption. The transdermal composition that are the subject of the present invention allow the achievement of:

a) a thermodynamic medicament activation, due to its incorporation, by an original process, into crosslinked or microporous microspheres, with the resulting destructuration of the drug crystalline structure;

b) the protection of the medicament from direct contact with the filmogenic polymeric mass, with the resulting higher chemical compatibility (lower degradability of the medicament, quicker crosslinking reaction when crosslinked polymeric matrices are used) and physical compatibility (maintenance of, the adhesive features of the polymeric mass, maintenance of the thermodynamic activation of the medicament, i.e. of its amorphous state);

c) improved shelf stability of the medicament's chemical-physical structure based on its inclusion into the micropores or within the internodal spaces of the particles;

d) the feasibility of including into the microparticles, in addition to the active agent, further substances such as "promoters of the cutaneous absorption". This term includes all those agents which are able to increase the uptake of the medicament through the skin. Among said agents, the following are cited: solvents such as dimethylsulfoxide, ethanol, azone, urea, etc; polyethlenegly of different molecular weights; fatty acids such as linoleic acid, vaccinic acid, oleic acid, etc; fatty acid esters as such isopropylmyristate (IPM), decyl oleate (CELTOL), ect; glycolic ester of fatty acids such as propyleneglycol dicaprylate/dicaproate (LEXOL PG 865), etc; triglycerides of fatty acids such as that of caproic acid (MYRITL 318), ect. Hitherto, said "absorption promoter" agents were directly dispersed within the mass of the transdermal polymeric matrix which may give rise to possible problems regarding the adhesiveness and chemical stability of the same (namely incompatibility between the filmogenic polymer and the promoter agent); moreover should the preparing process of the transdermal film be based on a crosslinking reaction, the presence of the promoter agent may delay or even completely hamper said reaction. Therefore, the possibility of including the absorption promoting agents into the crosslinked or microporous polymeric microparticles of the present invention removes all the aforementioned drawbacks and allows transdermal systems comprising both medicament and absorption promoting agents to be more easily obtained. In the case in which the microparticles are loaded with the promoter only, the drug will be dispersed in the polymeric matrix or vice versa. It is obviously also feasible either to load a part of the microparticles with the drug and a part with the absorption promoter (in the most suitable percentage) or to load both drug and promoter on the same particle. The transdermal compositions of the present invention consist of:

a) a supporting rigid layer (for instance polyethylene, polyesters, aluminum etc.);

b) a polymeric matrix in which the medicament loaded particles are dispersed, wherein said polymeric matrix consists of siliconic or acrylic adhesive polymers (the former used as organic solution the latter as aqueous dispersion) or of non adhesive polymers such as crosslinked polydimethylsiloxan or acrylic/methacrylic esters;

c) an adhesive membrane, when non-adhesive polymers are used only;

d) a removable protecting sheet.

The particles whereupon the medicament is loaded consist of microporous particles (such as silica gel, aluminum sesquioxide etc.) or of hydrophilic crosslinked polymeric microparticles (crosslinked polyvinyl-pyrrolidone, polymeric cyclodextrin, etc.).

DESCRIPTION OF THE DRAWING

The compositions are illustrated in FIG. 1 wherein:

(1)=impermeable supporting sheet;

Figure 1:
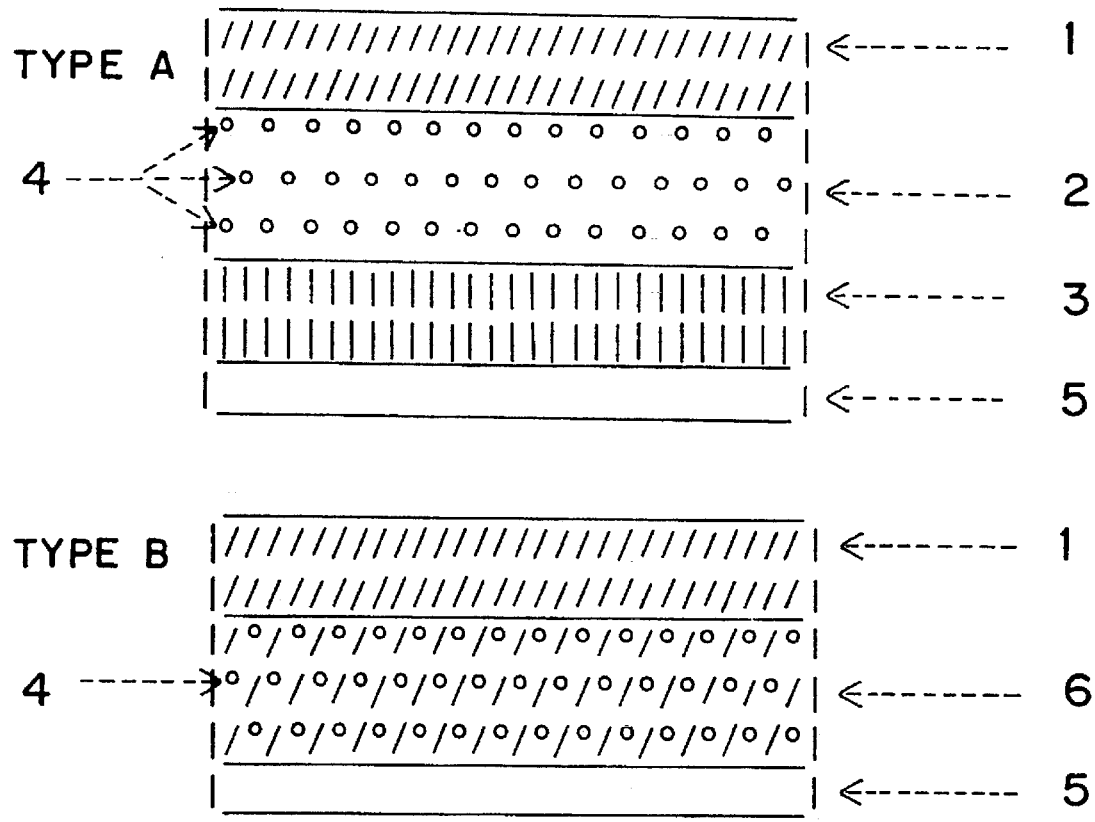

(2)=(non adhesive) polymeric matrix;

(3)=adhesive membrane;

(4)=microporous particles or polymeric microspheres loaded with the medicament and/or the promoter of cutaneous absorption;

(5)=protecting sheet to peel up;

(6)=(adhesive) polymeric matrix.

FIG. 1, type A illustrates the transdermal therapeutic compositions of the present invention wherein the polymeric matrix (2) is a non-adhesive polymer and an adhesive layer (3) is disposed between the polymeric matrix (2) and a protective removable sheet (5).

FIG. 1, type B illustrates the transdermal therapeutic compositions of the present invention wherein the polymeric matrix (6) itself is an adhesive polymer, covered by a protective removable sheet (5).

The process fop preparing the transdermal compositions of the present invention consists of the following stages:

1) the medicament of interest is dissolved in a suitable solvent, which may itself be a promoter of cutaneous absorption, and loaded on microporous particles (such as silica-gel, aluminum sesquioxide, etc), according to the technique disclosed in the Italian patent application 20145 A/88; as a further option the medicament is loaded on crosslinked polymeric microparticles (crosslinked polyvinylpyrrolidone, polymeric cyclodextpin, etc) by swelling with solutions and exposing to solvent vapors as described in the Italian patent application 22336 A/88 or by high power co-milling in presence of vapours as disclosed in the Italian patent application 22770 A/88.

2) The particles loaded with the medicament and/or with the absorption promoter, obtained in the previous stage, are thereafter dispersed in the mass of the filmogenic polymer which forms the transdermal system matrix, by making use of a suitable mixer under a vacuum.

3) The fluid polymeric mass including the dispersed particles is laid on a supporting rigid sheet (for instance polyethylene, polyesters, aluminum, etc.) with an adjustable thickness spreader.

4) The thus prepared film is put in a vacuum oven, at a temperature optimal either for evaporating the solvent, or for accomplishing the crosslinking reaction.

5) The thus obtained transdermal film may finally be further coated with either an adhesive film, should the first one not be adhesive, or merely with a protective sheet.

Nonlimitative examples of medicament classes are: analgesics, antiphlogistics, anesthetics, antihypertensives, ACE-inhibitors, antipyretics, bronchodilators, contraceptives, cardiovasculars, calcium-agonist, antidepressives, diuretics, hypnotics, hormonals, hyperglycemizers, psychic energetics, sedatives, tranquilizers, etc.

Nonlimitative examples of medicaments are: procatherol, salbutamol and the like, digoxin, chlorpropamid, allopurinol, indomethacin, naproxen, sulindac, indoprofen, piroxicam and the like, propranolol, atenolol, timolol, cimetidine, clonidine, levodopa, ketoprofen, alloperidol, diazepan, oxazepan, lorazepan, temazepan and the like, progestinics, estrogenics, progestactives, progesterone hydrocortisone, hydrocortisone acetate, cortisone acetate, triamcinolone, ciproterone, methylestrone, 17-β-estradiol, ethinylestradiol, norgestrol, norethylnodrel, medroxyprogesterone acetate, megestrol acetate and the like, nitroglicerine, nicergoline, nifedipine, nicardipine and the like, diltiazem, verapamil, peptide or polypeptide drugs such as calcitonin, somatostatin, LHRH, LHRH-analogs, etc. For illustrative purpose, the following nonlimitative examples of preparation of compositions according to the present invention are reported. The features are reported at the end of the examples.

EXAMPLE 1

950 mg crospovidone are loaded in a mortar with 2 ml of a solution of 95 mg/ml nifedipine in methylene chloride.

The product is dried in a vacuum oven at 30° C. for 1 hour. The thus obtained agglomerate is crumbled, sieved with a 60 mesh sieve and exposed for 24 hours to a methylene chloride atmosphere in a exsiccator (saturated atmosphere). The obtained agglomerate is crumbled again and vacuum dried at room temperature For 48 hours. The thus obtained loaded product shows a nifedipine/crospovidone ratio of 1:5 parts by weight. 9 g siliconic polymer MDX 4-4210 Dow Corning are mixed with 1 g of crosslinking agent. To said mixture 0.53 g of the product loaded with nifedipine/crospovidone 1:5 parts by weight are added and further homogenized in a mortar. The mixture is then poured into molds of polyethylene-polyvinylacetate copolymer, 18 mm in diameter; the mixture is degassed in a vacuum for about 15 minutes and maintained in a oven at 50° C. for 24 hours to complete the crosslinking reaction of the polymer. The amount of nifedipine is 0.8% by weight.

EXAMPLE 2

950 mg crospovidone are loaded in a mortar with 2 ml of a solution of 95 mg/ml of the medicament nicergoline in methylene chloride.

The product is dried in a vacuum oven at 30° C. for 1 hour. The thus obtained agglomerate is crumbled, sieved with a 60 mesh sieve and exposed for 24 hours to a methylene chloride atmosphere in a exsiccator (saturated atmosphere). The obtained agglomerate is crumbled again and vacuum dried at room temperature for 48 hours. The thus obtained loaded product shows a nicergoline/crospovidone ratio of 1:5 parts by weight. 9 g siliconic polymer MDX 4-4210 Dow Corning are mixed with 1 g of crosslinking agent. To said mixture 0.53 g of the product loaded with nicergoline/crospovidone 1:5 parts by weight are added and further homogenized in a mortar. The mixture is then poured into molds of polyethylene-polyvinylacetate copolymer, 18 mm in diameter; the mixture is degassed in a vacuum for about 15 minutes and maintained in a oven at 58° C. for 24 hours to complete the crosslinking reaction of the polymer. The amount of nicergoline is 0.8% by weight.

EXAMPLE 3

950 mg crospovidone are loaded in a mortar with 2 ml of a solution of 95 mg/ml of the medicament nicergoline in methylene chloride and 760 mg of the absorption promoter isopropylmyristate.

Methylene chloride is firstly removed by maintaining the product in a vacuum oven at 30° C. for 15 minutes, then for 24 hours at room temperature. The thus obtained agglomerate is crumbled and sieved with a 60 mesh sieve.

The thus obtained loaded product shows a nicergoline/isopropylmyristate/crospovidone ratio of 1:4:5 parts by weight. Siliconic polymer MDX 4-4210 Dow Corning (9 g) is mixed with 1 g of crosslinking agent. To said mixture 0.88 g of the product loaded with nicergoline/isopropylmyristate/crospovidone 1:4:5 parts by weight are added and further homogenized in a mortar. The mixture is then poured into molds of polyethylene-polyvinylacetate copolymer, 18 mm in diameter; the mixture is degassed in a vacuum for about 15 minutes and maintained in a oven at 58° C. for 24 hours to complete the crosslinking reaction of the polymer. The amount of nicergoline and isopropylmyristate are respectively 0.8% and 3.2% by weight.

EXAMPLE 4

950 mg crospovidone are loaded in a mortar with 2 ml solution of 95 mg/ml of the medicament nicergoline in methylene chloride. The product is dried in a vacuum oven at 30° C. for 1 hour. The thus obtained agglomerate is crumbled, sieved with a 60 mesh sieve and exposed for 24 hours to methylene chloride atmosphere in a exsiccator (saturated atmosphere). The obtained agglomerate is crumbled again and vacuum dried at room temperature for 48 hours. The thus obtained loaded product shows a nicergoline/crospovidone ratio of 1:5 parts by weight. Siliconic polymer MDX 4-4210 Dow Corning (9 g) are mixed with 1 g of crosslinking agent. To said mixture 0.53 g of the product loaded with nicergoline/crospovidone 1:5 parts by weight and 0.35 g isopropylmyristate are added by homogenizing in a mortar. The mixture is then poured into molds of polyethylene-polyvinylacetate copolymer, 18 mm in diameter; the mixture is degassed in a vacuum for about 15 minutes and maintained in a oven at 58° C. for 24 hours to complete the crosslinking reaction of the polymer. The amount of nicergoline and isopropylmyristate are respectively 0.8% and 3.2% by weight.

EXAMPLE 5

950 mg crospovidone are loaded in a mortar with 2 ml of a solution of 95 mg/ml of the medicament nicergoline in methylene chloride. The product is dried in a vaccuum oven at 30° C. for 1 hour. The thus obtained agglomerate is crumbled, sieved with a 60 mesh sieve and exposed for 24 hours to a methylene chloride atmosphere in a exsiccator (saturated atmosphere). The obtained agglomerate is crumbled again and vacuum dried at room temperature for 48 hours.

The thus obtained loaded product shows a nicergoline/crospovidone ratio of 1:5 parts by weight. Acrylic polymer 7927/79 Röhm-Pharma (16.7 g) (aqueous suspension with 60% dry residue) and 0.53 g of the product loaded with nicergoline/crospovidone 1:5 parts by weight are put into a vessel and mixed for 10 minutes. The mixture is then poured into molds of polyethylene-polyvinylacetate copolymer, 18 mm in diameter and maintained in an oven at 50° C. for 24 hours to obtain the solid matrix. The amount of nicergoline is 0.8% by weight.

EXAMPLE 6

950 mg crospovidone are loaded in a mortal with 2 ml solution of 95 mg/ml of the medicament nicergoline in methylene chloride. The product is dried in a vacuum oven at 30° C. for 1 hour. The thus obtained agglomerate is crumbled, sieved with a 60 mesh sieve and exposed for 24 hours to methylene chloride atmosphere in an exsiccator (saturated atmosphere). The obtained agglomerate is crumbled again and vacuum dried at room temperature for 48 hours.

The thus obtained loaded product shows a nicergoline/crospovidone ratio of 1:5 parts by weight. Siliconic polymer BIO-PSA 355 Dow Corning (solution in FREON at 18% by weight) (54 g) and (53 g) of the product loaded with nicergoline/crospovidone 1:5 parts by weight are brought into a vessel and mixed for 15 minutes allowing part of the FREON to evaporate. The mixture is then poured onto a suitable membrane of plastic material with or without an aluminum outer layer and the film is laid with a suitable spreader. As a spreader a bar is used which allows controlled thickness films to be obtained. The amount of nicergoline is 0.8% by weight.

EXAMPLE 7

20 g siliconic polymer BIO-PSA X7-3045 are mixed with 0.1 g crospovidone; the mixture is then poured on a supporting membrane (Scotchpack 1006 3M) into polyethylene molds, 5 cm in diameter, and maintained for 24 hours in oven at 40° C. to obtain a solid product. The amount of crospovidone is 1% by weight.

EXAMPLE 8

20 g siliconic polymer BIO-PSA X7-3045 are mixed with 0.53 g crospovidone and further processed as according to example 7. The amount of crospovidone is 5% by weight.

EXAMPLE 9

20 g siliconic polymer BIO-PSA X7-3045 are mixed with 1.11 g crospovidone and further processed as according to example 7. The amount of crospovidone is 10% by weight.

EXAMPLE 10

20 g siliconic polymer BIO-PSA X7-3072 are mixed with 0.1 g crospovidone; the mixture is then poured on a supporting membrane (Scotchpack 1006 3M) into polyethylene molds, 5 cm in diameter, and maintained for 24 hours in oven at 40° C. to obtain a solid product. The amount of crospovidone is 1% by weight.

EXAMPLE 11

20 g siliconic polymer BIO-PSA X7-3072 are mixed with 0.53 g crospovidone and further processed as according to example 10. The amount of crospovidone is 5% by weight.

EXAMPLE 12

20 g siliconic polymer BIO-PSA x7-3072 are mixed with 1.11 g crospovidone and further processed as according to example 10. The amount of crospovidone is 10% by weight.

EXAMPLE 13

9.50 g silica gel and 1.90 g of the medicament nicergoline are comilled in the milling chamber of a hight energy vibration mill, saturated with methylene chloride vapour.

The powdered product is dried, crumbled in a mortar and sieved with a 60 mesh sieve. The thus obtained loaded product shows a nicergoline/silica gel ratio of 1:5 parts by weight. 9 g siliconic polymer MDX 4-4210 Dow Corning are mixed with 1 g of crosslinking agent. To said mixture, 0.53 g of the product loaded with nicergoline/silica gel 1:5 parts by weight are added and homogenized in mortar. The mixture is then poured into molds of polyethylene-polyvinylacetate copolymer, 18 mm in diameter; the mixture is degassed in a vaccuum for about 15 minutes and maintained in an oven at 58° C. for 24 hours to complete the crosslinking reaction of the polymer. The amount of nicergoline is 0.8% by weight.

EXAMPLE 14

950 mg crospovidone are loaded in a mortar with 475 mg of the absorption promoter isopropylmyristate.

The product is sieved with a 60 mesh sieve. Thus obtained loaded product shows a isopropylmyristate/crospovidone ratio of 1:2 parts by weight. Siliconic polymer MDX 4-4210 Dow Corning (9 g) are mixed with 1 g of crosslinking agent. To said mixture, 0.09 g of nicergoline and 1.05 g of the product loaded with isopropylmyristate/crospovidone 1:2 parts by weight are added by homogenizing in mortar. The mixture is then poured into molds of polyethylene-polyvinylacetate copolymer, 18 mm in diameter; the mixture is degassed in vacuum for about 15 minutes and maintained in oven at 58° C. for 24 hours to complete the crosslinking reaction of the polymer. The amount of nicergoline and isopropylmyristate are respectively 0.8% and 3.2% by weight.

The following examples of compositions prepared according to known techniques are hereinafter reported to allow a comparison with the aforementioned examples.

EXAMPLE A 9 g of the sillconic polymer MDX 4-4210 Dow Corning are mixed with 1 g of crosslinking agent. Crystalline nifedipine (0.81 g) and a few ml of methylene chloride are added and the mixture homogenized in a mortar. The methylene chloride is allowed to evaporate in the air under an aspirating hood; the mixture is then poured into copolymer polyethylene-polyvinylacetate molds, 18 mm in diameter, degased in a vacuum for about 15 minutes and maintained in an oven at 50° C. for 24 hours to complete the crosslinking reaction of the polymer. The amount of nifidipine is 0.8% by weight.

EXAMPLE B 9 g of the siliconic polymer MDX 4-4210 Dow Corning are mixed with 1 g of crosslinking agent. Crystalline nicergoline (0.81 g) and a few ml of methylene chloride are added and the mixture homogenized in mortar. The methylene chloride is allowed to evaporate; the mixture is then poured into copolymer polyethylene-polyvinylacetate molds, 18 mm in diameter, degased in a vacuum for about 15 minutes and maintained in an oven at 58° C. for 24 hours to complete the crosslinking reaction of the polymer. The amount of nicergoline 0.8% by weight.

EXAMPLE C 9 g of the siliconic polymer MDX 4-4210 Dow Corning are mixed with 1 g of crosslinking agent. Crystalline nicergoline (0.81 g), isopropylmyristate (0.33 g) and a few ml of methylene chloride are added and homogenized in a mortar. The methylene chloride is allowed to evaporate; the mixture is then poured into copolymer polyethylene-polyvinylacetate molds, 18 mm in diameter, degassed in a vacuum for about 15 minutes and maintained in an oven at 58° C. for 24 hours to complete the crosslinking reaction of the polymer. The amount of nicergoline and isopropylmyristate are respectively 0.8% and 3.2% by weight.

EXAMPLE D 16.7 mg acrylic polymer 7927/79 Röhm-Pharma (aqueous suspension with 60% dry residue), crystalline nicergoline and a few milliliters ethanol 95% are brought into a beaker and mixed for 10 minutes. The mixture is then poured into polyethylene-polyvinylacetate and kept in oven at 50° C. for 24 hours to obtain the solid matrix. The amount of nicergoline is 0.8% by weight.

EXAMPLE E 54 g of siliconic polymer BIO-PSA 355 Dow Corning (solution in FREON at 18% by weight) and 0.081 g of crystalline nicergoline are brought into a vessel and mixed for 15 minutes, allowing part of the freon to evaporate. The mixture is then poured onto a suitable membrane of plastic material, with or without aluminum outer layer and the film is laid with a suitable spreader. As a spreader a bar is used which allows controlled thickness films to be obtained. The amount of nicergoline is 0.8% by weight.

EXAMPLE F 20 g siliconic polymer BIO-PSA X7-3045 (hexane solution 50% by weight) are poured on a support membrane (Scotchpack 1006 3M) into polyethylene molds, 5 cm in diameter and kept in oven at 40° C. for 24 hours to obtain the solid product. Finally the protective membrane (Scotchpak 1022 3M) is laid on it.

EXAMPLE G 20 g siliconic polymer BIO-PSA X7-3072 (hexane solution 50% by polyethylene molds, 5 cm in diameter and kept in an oven at 40° C. for 24 hours to obtain the solid product. Finally, the protective membrane (Scotchpak 1022 3M) is laid on it.

CHARACTERIZATION TESTS

There are illustrated hereinafter the description and the results of the characterization tests of the compositions according to the invention and comparative tests on analogous compositions obtained according to the known technique.

1. Release Test

The mold containing the siliconic matrix is weighed and the weight of the empty mold is subtracted in order to derive the weight of the matrix. The mold is attached to the bottom of a watch-glass using an adhesive tape or siliconic glue. In this way, one surface only of the matrix is exposed to the receiving solution. The watch-glass is then covered with a net held solid to the same by plastic clips or adhesive tape. The watch-glass is brought into a releasing vessel held in a thermostated bath at 37° C. Then 250 ml of the previously thermosrated receiving solution (acetate buffer pH 5.5) are added. The stirring propeller is placed at 2.5 cm from the mold and rotated at 50 rpm. 4 ml aliquots of the receiving solution are collected at fixed periods of time and immediately replaced by new buffer solution (pH 5.5), pre-heated at 37° C. A spectrophotometric monitoring is carried out by reading the absorbance at the wavelength of 284 nm. The crosslinked siliconic matrixes MDX 4-4210 release the nifedipine loaded on crospovidone quicker than the crystalline nifedipine. This is illustrated by the results reported in Table 1.

TABLE 1

Percentage of crospovidone-loaded or crystalline nifedipine released from crosslinked MDX 4-4210 matrixes:

| time | % nif./crosp. example 1. | % nif.cryst. example A |
|---|---|---|
| 2h 30' | 20.5 | 11.7 |
| 5h 00' | 23.0 | 10.2 |
| 7h 30' | 23.3 | 12.0 |
| 23h 00' | 27.9 | 17.2 |
| 31h 30' | 34.1 | 20.3 |

2. Test of Crosslinkage Extent

Two semiquantitative tests have been applied in order to determine the crosslinkage extent and the technological effectiveness of the siliconic matrixes MDX 4-4210 and corresponding crosslinking agent. The tests consist of monitoring the variation in viscosity, i.e. in firmness of the matrice with the time. In the first test the matrix is put on a nearly vertical smooth surface and the sliding in a fixed period of time is recorded. In the second test a weight is loaded at determinated times on the surface of the matrix and observed to ascertain whether or not it sinks into the matrix, and the extent of the sinking is evaluated. Evidence of the crosslinkage extent of the matrix is obtained in this way and may be summarized as follow:

1. no crosslinking;
2. insufficient crosslinking;
3. sufficient crosslinking;
4. moderate crosslinking;
5. effective crosslinking;
6. complete crosslinking.

The siliconic matrices MDX 4-4210 with crosslinking agent get crosslinked quicker when they are mixed with crospovidone-loaded nicergoline than when they are mixed with crystalline nicergoline. This is evident from the data reported in Table 2.

TABLE 2

Crosslinkage of MDX 4-4210 with crosslinking agent in presence of crospovidone-loaded nicergoline or crystalline nicergoline.

| temperature (C.°) | time (hours) | nic./crosp. (example 2) | nic.cryst. (example B) |
|---|---|---|---|
| 50 | 24 | 4 | 1 |
|  | 72 | 5 | 2 |
|  | 120 | 6 | 3 |
|  | 168 | 6 | 4 |
| 58 | 12 | 5 | 3 |
|  | 24 | 6 | 4 |
|  | 36 | 6 | 6 |
| 62 | 3 | 4 | 3 |
|  | 6 | 5 | 4 |
|  | 24 | 6 | 5 |
| 75 | 6 | 6 | 5 |
|  | 24 | 6 | 6 |

The crosslinkage speed of the MDX 4-4210 siliconic matrices with crosslinking agent, nicergoline and isopropylmyristate decreases in the order: nicergoline and isopropylmyristate loaded on crospovidone, nicergoline loaded on crospovidone and isopropylmyristate dispersed within the matrix, crystalline nicergoline and isopropylmyristate dispersed within the matrix. This is evident from the data reported in table 3.

TABLE 3

Crosslinking of MDX 4-4210 with crosslinking agent in presence of nicergoline and isopropylmyristate loaded on crospovidone, nicergoline loaded on crospovidone and isopropylmyristate, crystalline nicergoline and isopropylmyristate; Temperature 58°C.

| time (h) | nic.IPM./ crosp. (example 3) | nic./crosp. IPM (example 4) | nic.cryst. IPM (example C) |
|---|---|---|---|
| 5 | 5 | 4 | 3 |
| 18 | 6 | 5 | 4 |
| 24 | 6 | 6 | 5 |

3. Technological Tests on Bioadhesive Films

The technological features of the bioadhesive films prepared from the tested siliconic polymers BIO-PSA, are the detachment of the protective sheet, the adherence and the adhesiveness. The first test is carried out as follows. A small part of the protective membrane is gently detached from the polymeric substrate. The two edges are fastened with the instrument clamps which are shifted at a detaching speed of 101 cm/min. The clamps are moved in the same direction though along the two opposite sites. The curve strength versus time necessary to achieve the detachment is then recorded. The second test is carried out as follows: After having very gently removed the protective membrane from the polymeric substrate, this is deposited on a smooth, clean stainless steel surface. The film is forced to adhere to the surface by means of a 2 Kg roller, keeping, however an edge free to be fastened with the clamp placed at 90° with regard to the same. The clamp is shifted at the speed of 30.5 cm/min and the curve strength versus time is recorded to determine the adherence. The third test is carried out as follows: A piece of film 2.5 cm×2.5 cm in size is cut, the protective membrane is gently removed from it, and then it is located in the suitable chamber of the instrument to test the adhesiveness. The monitoring is carried out by keeping the film in contact with the adhesion surface for 1 second and fixing a detachment speed of 10 mm/min. The curve strength versus time is recorded to determine the adhesiveness. The results reported in Table 4 point out that the presence of crospovidone within the matrices of bioadhesive polymers BIO-PSA does not modify the technological features (detachment of the protective sheet, adherence and adhesiveness) of the same. On the contrary the presence of crospovidone improves the adhesiveness of the matrices of bioadhesive polymer BIO-PSA X7-3045.

TABLE 4

Technological features of bioadhesive siliconic polymers BIO-PSA mixed with crospovidone.

| BIO-PSA | crosp. % weight | detach. | adher. | adhesiv. |
|---|---|---|---|---|
| X7-3045 (ex.F) | 0 | 1 | 2 | 3 |
| X7-3072 (ex.G) | 0 | 1 | 2 | 2 |
| X7-3045 (ex.9) | 10 | 1 | 2 | 2 |
| X7-3045 (ex.8) | 5 | 1 | 2 | 2 |
| X7-3045 (ex.7) | 1 | 1 | 2 | 2 |
| X7-3072 (ex.12) | 10 | 1 | 3 | 2 |
| X7-3072 (ex.11) | 5 | 1 | 2 | 2 |
| X7-3072 (ex.10) | 1 | 1 | 2 | 2 |

Detachment of the protective sheet:
1 = very easy;
2 = easy;
3 = sufficient;
4 = difficult;
5 = no detachment.
Adherence and adhesiveness:
1 = optimum;
2 = effective;
3 = sufficient;
4 = insufficient;
5 = none.

4. Technological Features of the Acrylic Matrices

The acrylic matrixes from 7927/79 (example 5 and example D) are more easily prepared and offer a better final product in presence of nicergoline loaded on crospovidone as compared to crystalline nicergoline. In the presence of crystalline nicergoline, a net separation of the same nicergoline, which tends to sediment on the bottom of the vessel, and the polymeric suspension is observed. Matrices comprising non-homogeneous nicergoline concentrations are thus obtained. Should the nicergoline tentatively be solubilized with water soluble organic solvents such as methanol, ethanol, etc., a sticky unmanageable mixture is obtained, which is due to a solvent/suspendent interaction and which cause the acrylic polymer to collapse. In the presence of crospovidone-loaded nicergoline, the polymeric suspension is homogeneous and also more easily mixable, since it is less viscous than the previous one.

5. Determination of the Crosslinkage Kinetic by Means of D.S.C.

The suitable amounts of polymer, crosslinking agent and medicament (either loaded or not) are mixed, an aliquot of 15–20 mg is weighed and brought into the cell of a differential scanning calorimeter 7-Perkin Elmer. The determination is carried out within the temperature range 30°–160° C. at thermic scanning speed of 10° C./min. At the end of the analysis a specific software program allows the data concerning the time for the complete achievement of the crosslinking reaction to be directly obtained, as reported in Table 5, or also the data concerning the lowest temperature necessary for the complete achievement of the crosslinking reaction within 24 hours, as reported in Table 6.

The results reported in said tables point out that a complete crosslinkage in presence of crospovidone-loaded nicergoline is performed in a definitively shorter period of time when compared to the nicergoline as such, or that a clearly lower temperature is sufficient to obtain a complete crosslinkage in a prefixed period of time.

TABLE 5

Time (hours) to achieve the complete crosslinkage of films of MDX 4-4210 comprising either nicergoline or crospovidone-loaded nicergoline at different temperatures. The mark (—) means that the complete crosslinkage is achieved after 24 hours.

|  | 50° C. | 58° C. | 65° C. |
|---|---|---|---|
| nic. cryst. (ex.B) | — | 22.30 | 6.45 |
| nic./crosp. (ex.2) | 13.15 | 4.45 | 2.00 |

TABLE 6

Lowest temperature necessary for the complete crosslinkage of films of MDX 4-4210 comprising either nicergoline or crospovidone-loaded nicergoline within 24 hours.

| nic.cryst. (ex.B) | 59° C. |
|---|---|
| nic./crosp. (ex.2) | 46° C. |

We claim:

1. A transdermal therapeutic composition consisting of a supporting rigid sheet, a polymeric matrix selected from the group consisting of silicon adhesive polymers, acrylic adhesive polymers, crosslinked polydimethylsiloxane and acrylic/methacrylic esters and a protective removable sheet, wherein said polymeric matrix consists of a polymeric film in which there are distributed microparticles selected from the group consisting of microporous particles of silica gel or aluminum sesquioxide and hydrophilic, crosslinked, polymeric microparticles selected from the group consisting of crosslinked polyvinyl pyrrolidone and polymeric cyclodextrin, in or on which are loaded medicaments and agents for promoting cutaneous absorption selected from the group consisting of dimethylsulfoxide, ethanol, azone, urea, polyethylene glycols, fatty acids and fatty acids esters.

2. The transdermal therapeutic composition according to claim 1, wherein one portion of said microparticles is loaded with said medicaments and the other portion of said microparticles is loaded with said agents for promoting cutaneous absorption.

3. The transdermal therapeutic composition according to claim 1, wherein said polymeric matrix consists of an adhesive siliconic polymer.

4. The transdermal therapeutic composition according to claim 1, wherein said polymeric matrix consists of an adhesive acrylic polymer.

5. The transdermal therapeutic composition according to claim 1, wherein said polymeric matrix consists of crosslinked polydimethylsiloxane.

6. The transdermal therapeutic composition according to claim 1, wherein said polymeric matrix consists of acrylic esters.

7. The transdermal therapeutic composition according to claim 1, wherein said polymeric matrix consists of methacrylic esters.

8. The transdermal therapeutic composition according to claim 1, wherein said microporous particles consist of silica gel.

9. The transdermal therapeutic composition according to claim 1, wherein said microporous particles consist of aluminum sesquioxide.

10. The transdermal therapeutic composition according to claim 1, wherein said polymeric hydrophilic crosslinked microparticles are crosslinked polyvinyl-pyrrolidone on which are loaded said medicaments.

11. The transdermal therapeutic composition according to claim 1, wherein said polymeric hydrophilic crosslinked microparticles are crosslinked polymeric cyclodextrin on which are loaded said medicaments.

12. The transdermal therapeutic composition according to claim 1, wherein said medicament is nifedipine.

13. The transdermal therapeutic composition according to claim 1, wherein said medicament is nicergoline.

14. A process for preparing a transdermal therapeutic composition consisting of a supporting rigid sheet, a polymeric matrix selected form the group consisting of siliconic adhesive polymers, acrylic adhesive polymers, crosslinked polydimethylsiloxane and acrylic/methacrylic esters; and a protective removable sheet, wherein said polymeric matrix consists of a polymeric film in which there are distributed microparticles loaded with medicaments and with agents for promoting cutaneous absorption, comprising the following steps:

a) loading said medicament and said promotor for cutaneous absorption on microparticles;
   b) dispersing said loaded microparticles within the fluid mass of a filmogenic polymer;
   c) laying said fluid mass containing said dispersed loaded microparticles on a supporting rigid sheet by means of an adjustable thickness spreader;
   d) placing said sheet containing said laid fluid mass in an oven to evaporate solvent and to accomplish a crosslinking reaction; and
   e) optionally coating said sheet with an adhesive film and covering said optionally coated sheet with a protective removable sheet.

15. A transdermal therapeutic composition consisting of a supporting rigid sheet;
   a polymeric matrix selected from the group consisting of siliconic adhesive polymers, acrylic adhesive polymers, crosslinked polydimethylsiloxane and acrylic/methacrylic esters;
   microparticles loaded with medicaments;
   microparticles loaded with agents for promoting cutaneous absorption of said medicaments; and
   a protective, removable sheet;

wherein said microparticles are distributed in said polymeric matrix.

16. The transdermal therapeutic composition of claim 1, wherein said fatty acid esters are selected from the group consisting of glycolic esters of fatty acids and triglycerides of fatty acids.

17. A transdermal therapeutic composition according to claim 1, wherein said medicament and said agents for promoting cutaneous absorption are loaded on the polymeric microparticles by swelling and exposing to solvent vapours.

18. A transdermal therapeutic composition according to claim 1, wherein said medicament and said agents for promoting cutaneous absorption are loaded on the polymeric microparticles by high power comilling, in presence of solvent vapours.

19. A transdermal therapeutic composition according claim 1, wherein said medicament and said agents for promoting cutaneous absorption are loaded in the microparticles by adding microparticles into a solution containing said medicament and said agents for promoting cutaneous absorption under continuous stirring, and evaporating the solvent.

* * * * *